United States Patent [19]
Friedenberg et al.

[11] 3,947,328
[45] Mar. 30, 1976

[54] GLUCOSE LEVEL TEST METHOD

[76] Inventors: Robert M. Friedenberg, 8792 Oxwell Lane, Laurel, Md. 20810; John L. Yoscak, 2893 Balmoral Drive, Rockville, Md. 20850; Stephen E. Noren, 1813 Mt. Pisgah Lane No. 124, Silver Spring, Md. 20903

[22] Filed: June 15, 1973

[21] Appl. No.: 370,238

[52] U.S. Cl.............. 204/1 T; 204/195 B; 23/230 B
[51] Int. Cl.²................. G01N 27/46; G01N 31/00
[58] Field of Search............ 204/1 T, 195 R, 195 B; 23/230 B

[56] References Cited
UNITED STATES PATENTS

| | | |
|---|---|---|
| 3,298,934 | 1/1967 | Angeleri.............................. 204/1 T |
| 3,770,607 | 11/1973 | Williams............................. 204/1 T |

OTHER PUBLICATIONS

National Bureau of Standards Special Pub. 314, Nov. 1969, pp. 367–371, 407 & 430.
Frant, "Plating", July, 1971, pp. 686–693.

*Primary Examiner*—T. Tung

[57] ABSTRACT

Method, apparatus and test compositions are provided for rapid, accurate test of concentration levels of various components of body fluids, particularly the glucose level in saliva, by oxidizing the test sample under controlled conditions with an excess of oxidizing agent and measuring the level of the component such as glucose in the body fluid as redox potential in millivolts of a primary cell in which the residual oxidizing solution is the electrolyte.

13 Claims, 6 Drawing Figures

U.S. Patent    March 30, 1976    Sheet 1 of 3    3,947,328
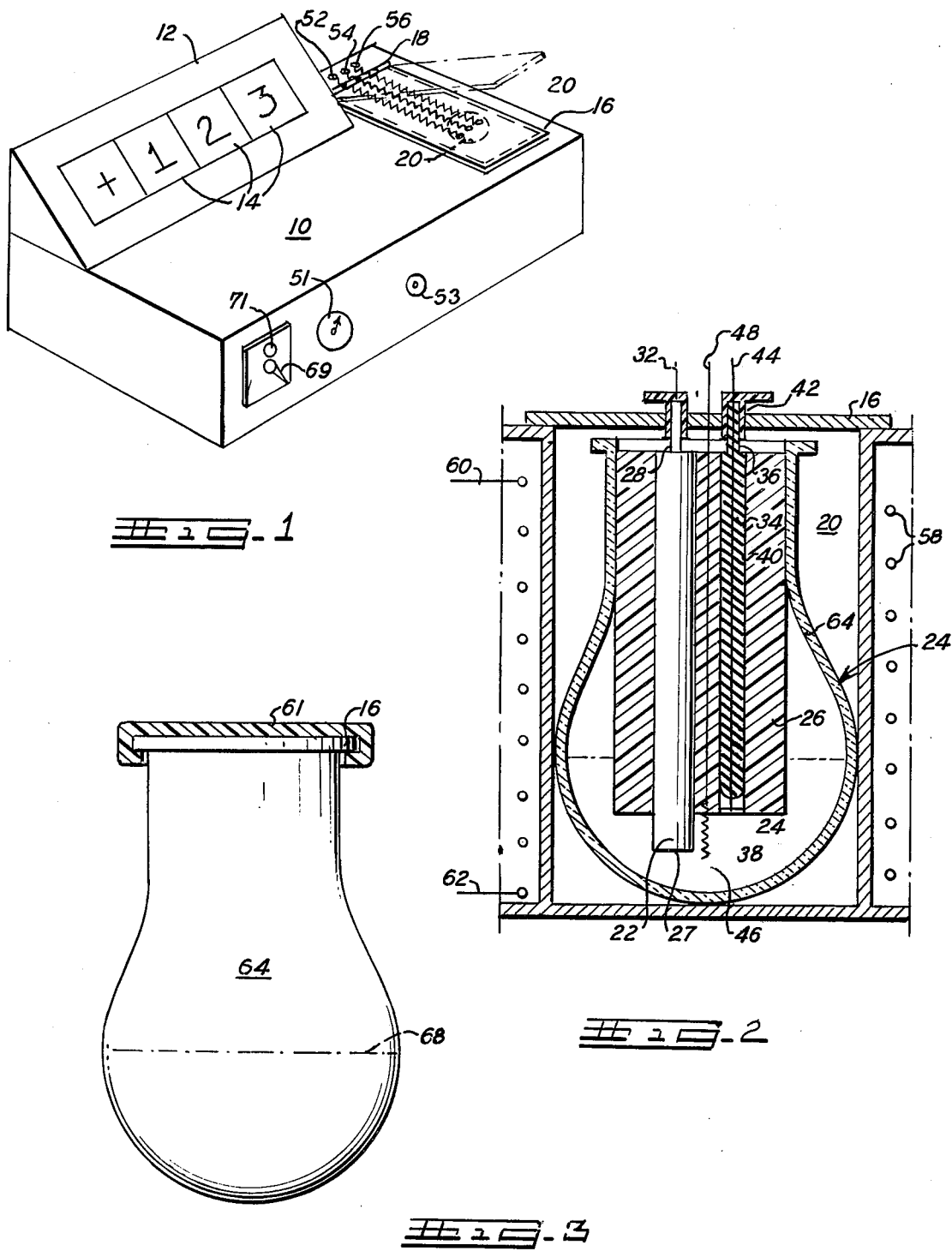

GLUCOSE LEVEL TEST METHOD

This invention relates to the method and apparatus for quantitative measurement of concentration levels of various components of body fluids such as glucose levels in any of the body fluids; and, more particularly, to measuring the human body fluid components such as glucose levels by measurement quantitatively of the residual oxidation-reduction potential of the reaction medium including the body fluid following chemical reaction with a small measured quantity of at least one reagent such as reducing or oxidizing agents; to an electrochemical redox potential measuring cell and apparatus with which the cell is used to provide an accurate read-out of the developed potential of such cell by the reacted body fluid sampling, simplified for rapid and easy use by individuals and professionals; and to appurtenant compositions and elements useful in operation of the apparatus and performing of the test.

There is a substantial prior art of continuing efforts to measure components of body fluids, such as the glucose level of small quantities of body fluid, but these are generally complicated, difficult and time consuming to perform, and are often inaccurate. Testing upon urine by prior methods has been largely colorometric and inaccurate; and with blood as well as urine, common chemical procedures for testing of the glucose level have been long, complex, time consuming, expensive and generally beyond the skill of non-professionals.

The present method is much superior in that it is accurate and much simplified for rapid and easy use by both laymen and professionals. It may be applied to any small measured quantity of any body fluid such as saliva, spinal fluid, perspiration, tears, whole blood, plasma or urine. This method is operative easily even upon the unusual body fluids in this list and the testing of the glucose level of fluids, even available only in small quantity, for example, in saliva, is quite rapid and accurate.

In broadest aspect, this invention is directed to a method of testing concentration levels of certain components of body fluids, particularly of glucose levels in body fluids, first by adequate sampling of the body fluid, in quantitatively oxidizing the glucose content thereof under fixed conditions, such as at a selected fixed temperature, such as the boiling point of water, for a short fixed time period, with a measured excess quantity of oxidizing solution; and then measuring electrochemically the residual quantity of oxidizing agent, whereby to measure the oxidized quantity of glucose present in the test sample by difference.

The present method for oxidizing agent typically uses a solution comprising a measured quantity of a divalent copper salt, such as a Benedict solution, with which the glucose content of the sampling is first completely oxidized at the expense of the measured quantity of oxidizing agent. The residual millivoltage developed by a primary cell using oxidized test sample and the partially reduced copper solution as electrolyte is then measured and the direct read-out can be used to indicate numerically, either the millivoltage or the exact glucose content of the test sample.

Thus, the glucose content of the primary cell output will be readable as a measurement in millivolts produced by the residual reduced copper salt content of the test solution as electrolyte.

In this manner, the glucose content of the body sampling is read negatively as the millivoltage developed in a primary cell using the residual quantity of the body fluid in which the glucose was oxidized together with the excess of unreduced oxidizing agent as the electrolyte. The quantity of glucose originally present in the sample reduces its corresponding quantity of oxidizing agent, for example, the divalent copper salt, thus modifying the electrical output of the cell in millivolts according to the original quantitative glucose presence, to give a cell output readable as proportional to the residual copper salt potential, indicative of the original glucose level that was oxidized. It may also be considered that the redox potential of the cell may be converted to be a direct reading of the original glucose content of the test sample. That relationship between millivolt output of the cell and the original glucose content of the test sample is set forth by the curve of FIG. 6.

In a second aspect of the invention, a test apparatus is provided, which may include a sample holding and treating means, a timed heating and temperature control means, means for supplying a measured test sample and reagent to the sample treating means, an electrode and cell components and circuitry for accurately measuring and indicating the residual potential of a reaction solution in which the glucose content of the sample was oxidized, electrical indicator means showing the results of the tests whereby they are directly readable for performing a very rapid glucose level test quantitatively, accurately, and even readable in numerical terms directly indicative of the glucose level of the sample.

Other elements of this invention comprise accurate quantitatively fixed reagent pills or tablets for supply of reagent to the reaction solution as a single pellet of premeasured quantity of reagent for the test, whereby individual measurement of chemical reagent in accurate quantity is not needed by the operator for the test; or alternately a premixed standard solution sealed in a throw-away reaction container having a wide mouth through which may be suspended the electrode assembly during the test; as well as pipette means for accurately measuring the sample of the body fluid for use in the test. This allows the total test to be easily performed rapidly and accurately by anyone, typically a laboratory technician, a physician performing a test in his own office upon a patient, or a patient himself applying the test in his own home periodically to know the glucose levels of his own body.

Accordingly, it is the object of this invention to provide the steps and apparatus elements as listed above to perform the invention described herein. Other objects are inherent.

The fundamental procedure as referred to above lies in the oxidation of an accurate sampling with a measured quantity of oxidizing agent such as a copper salt, typically a Benedict solution, but other oxidizing solutions including reducible copper solutions from which the residual copper salt may be measured electrimetrically may be used.

The quantitative Benedict solution is preferably the solution with which the glucose in the body fluid, such as saliva, reacts and uses the cupric ion ($Cu^{++}$) as the specific ion that undergoes a change in concentration. The actual measurement is made on the concentration of $Cu^{++}$ ions left in the solution after the glucose has reduced a portion of the $Cu^{++}$. There is a definite quantitative relationship between the amount of glucose present and the amount of $Cu^{++}$ that has been reduced. Thus by measuring the amount of $Cu^{++}$ ions left in solution, a quantitative reading of the amount of glucose that was present in the saliva is obtained. The theoretical relations governing a cell of this nature are approximately fixed by the Nernst Equation:

$$E = E_o - \frac{0.592}{N} \log \frac{C^c D^d}{A^a B^b}$$

for the reaction $aA + bB = cC + dD$. The only variable to be considered in this reaction is the Cupric ion ($Cu^{++}$). All the other variables are held constant and the electron exchange (N) is 2. Thus the equation simplifies to:

$$E = E_0 - 0.029 \log 1/Cu^{++} (Cu^{++} 1).$$

Hence, as the concentration of cupric ions decreases (more glucose reacting), the output voltage of the cell decreases logarithmically. This voltage change could be measured easily with a metallic electrode system and a voltmeter.

In brief preliminary description of the test method, a sampling, preferably saliva from the mouth of the test person, deposited in a cup in exact sampling quantity by being taken up quantitatively in a filter type pipette, as described below, and that measured quantity is transferred to a test container of any suitable shape such as a small test tube, bottle, chemical flask, beaker, or the like, together with a pipette quantity, 2 or 3 cc., of test solution, i.e., Benedict solution of standard strength, or an exact quantity of dry components in a pill, comprising a measured quantity of dry Benedict salt or other reducible copper salt is added to a measured quantity of 1 to 10 cc., usually 2 to 3 cc., of water. The container has the standard electrodes inserted therein to contact the solution. The electrodes are made part of a standardized circuit adjusted to a null voltage before start of the test. The test sample is inserted in the apparatus and is then heated for a time to an accurately controlled temperature. At the end of the timed period upon reaching the temperature and being heated for 10 to 20 seconds, the reading of the cell containing the residual of the liquids then appears on the dial, indicating the output voltage difference of the cell. That output voltage can be plotted graphically against the glucose contents of a range of samplings, whereby the glucose content can be graphically determined, or the indicator itself may be read numerically in terms of glucose content, millivolts or other numerical system intelligible to the reader, significant of the glucose level of the sample.

Reference is made to the drawings wherein:

FIG. 1 shows an assembled measuring device with a slot for receiving a test container and cell supporting means for a readout indicator for test results;

FIG. 2 is an enlarged detail of FIG. 1 showing the sample holding means, cell and electrodes therein;

FIG. 3 shows shows a disposable container;

Figure 4:
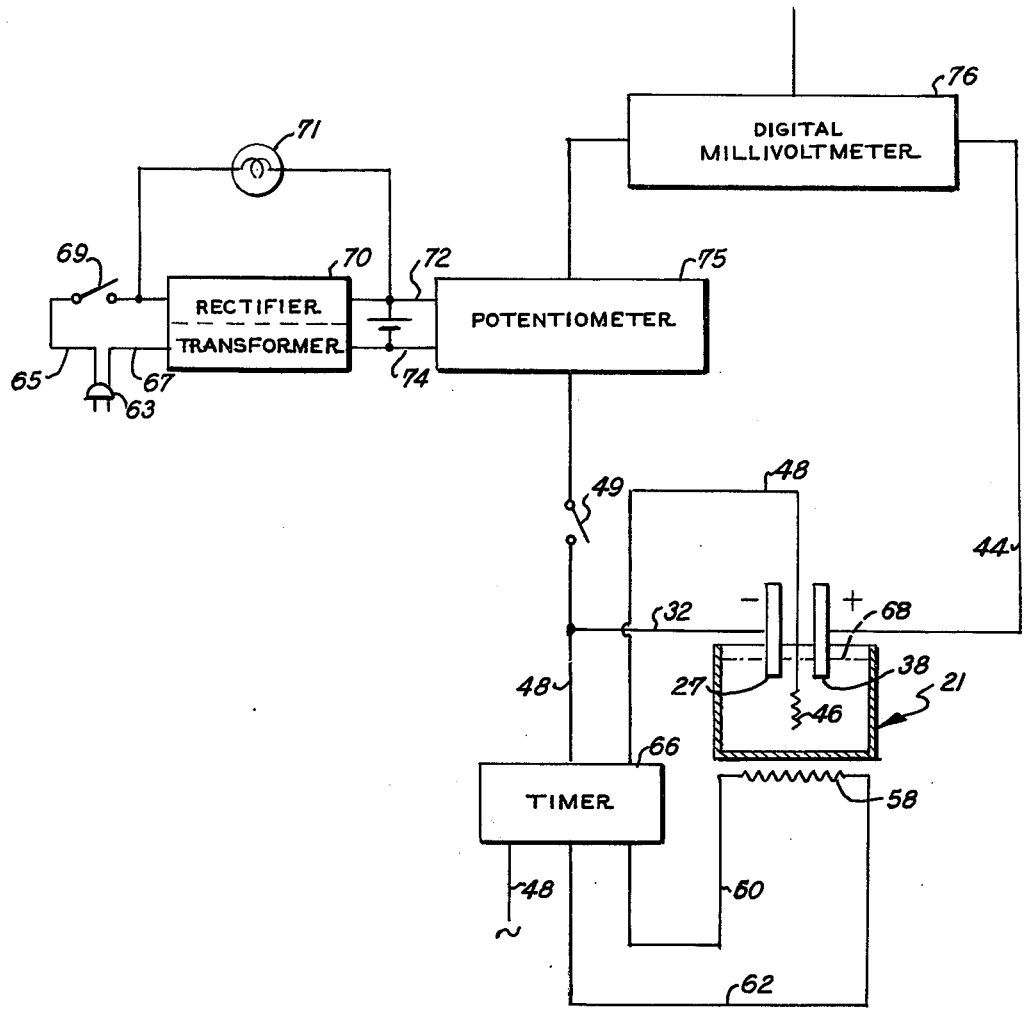
FIG. 4 shows an electrical operating circuit for the test device.

Referring first to FIG. 1, the test device comprises a housing 10 of attractive shape having a readout section 12 in which the results of tests are indicated numerically at 14 or by other indicia significant of glucose test quantity, representative of the tests, such as millivolts, or words such as "high", "low", or "medium", etc. Thus, other useful visible indicia significant of the results of the test may be substituted.

The housing 10 may have a test chamber 20 closed by a cover 16 hinged at one end to the upper housing surface 18, covering an annular, such as a cylindrical, test space. As shown in FIG. 2, the hinged cover 16 supports a pair of electrodes 22 and 24, encased as an assembly 26 in a colorless, transparent plastic such as crystal polystyrene. The electrode 22 is of a stable conductive metal, preferably as negative electrode of solid copper, and has its lower end 27 protruding a short distance below the plastic bottom as shown to expose a fixed electrode surface area. The electrode 22 terminates at its upper end in a jack-type plug 28 insertable in a jack-type spring metal clasp as receiver 30 to which it completes its electrical circuit to a conductor wire 32. The electrode 24 comprises a conductor wire 34 similarly sealed at its upper end into a jack-type metal plug 36 and at its lower end as positive electrode into a platinum plate 38, having a fixed surface area exposed through the bottom surface of the electrode assembly. Thus, both electrode ends 27 and 38 are separated by plastic and have a fixed exposed surface area. The electrode 34 is encased along its length in a rubber sheath 40 for resilient support of the fragile wire 34 which may be platinum. The upper end of the plug 36 similarly is a metal plug insertable in a flexible jack-type connector 42, which in turn is connected to a conductor wire 44.

An electrical sensor, a temperature sensitive coiled wire 46 extends from the bottom of the electrode casing 26 and passes through the plastic casing in which it is supported to conductor wire 48. The wire 46 acts as a temperature sensor of conventional construction and each of the three conductor wires 32 44 and 48 lead to contacts 52, 54 and 56, respectively, for transfer of their electrical currents of the circuit of FIG. 4 in the relationship as will appear below.

The annular wall 21 enclosing a test chamber 20 has electrical heating elements 58 mounted therein which are connected in circuit through lead wires 60 and 62 with a source of current for controlled heating of a test receptacle 64. A timer 66 of known construction is disposed in the circuit as shown to activate and deactivate the heating circuit to heating coils at the temperature controlled by the sensor 46 as will appear. That timer for present test purposes will time the heating current passed through heating elements 58 for a short fixed heating period, set for about 5 seconds up to about a minute, usually about 10 to 20 seconds.

The electrode assembly 26 connected in the circuit through the contacts 30 and 42 and supported in the cover 16 is inserted into the test container 64 with the exposed surface area of its electrodes in contact with the test solution 68 so that the electrical output of the cell will be read as the large visible indicia 14 in the test device.

The basic circuit, as shown in FIG. 4, comprises an outside source, i.e., a wall plug 63 which connects with a household current supply by way of lines 65 and 67, as controlled by an off-on switch 69, and usually an indicator light 71 to show that the circuit is activated.

The current passes first through a combination rectifier and transformer 70 which reduces the current to a selected low voltage such as less than about 10 volts usually of direct current which passes to a potentiometer 75 by way of lines 72 and 74 in which the current can be adjusted to null voltage for the circuit. The oxidizing Benedict solution has a minor voltage, less than a volt, and the internal circuitry also modifies the voltage reading. Consequently, the potentiometer is used to adjust the voltage condition of the circuit, including the cell 26 to a null voltage before test. With such initial adjustment, the digital volt meter 76 will then be read as the actual output voltage decreased of the cell 26, its electrode output developed from electrodes 32 and 34 using the reaction solution as electrolyte.

The generally closed test switch 49 activates the cell circuit by the lighted active circuit at 71. A knob 53 controls the potentiometer, thus, adjustable in the range of 0 to 1.5 volts, as is shown on dial 51, the operating circuit with the cell 26 to approximately a null voltage whereby the measurement of the reduced test solution in cell 26 is ready for reading. This is a true reading of the actual redox potential developed difference in the cell.

While current filling the transformer and rectifier is within the range of 0 to 1.5 volts, the potentiometer is used each time before test to set up the test and its reading will become the 0 point of measurement of the developed voltage by the cell 26. For this purpose the potentiometer may be about 10 kiloohms for use in conjunction with the 1.5 volt DC power supply whereby the potentiometer allows that DC voltage to be adjusted from any value ranging from 0 to 1.5 voltage and can be adjusted even over a very small voltage range of less than approximately 0.5 volts.

The temperature sensor 46 is capable of triggering the timing circuit when the test solution has reached the selected temperature, such as about the boiling point of water; for instance, 98°C plus or minus 2. Other standard temperature sensors may be substituted, such as a thermister. This temperature sensor contacts the test solution and triggers the timing circuit each time when the exact selected sensed temperature is reached.

The timing circuit functions to measure an exact time interval herein selected within the range stated above, for example, at about 15 seconds, and the temperature sensor starts the timer circuit when the selected temperature is reached, holding the same for the selected 15 seconds plus or minus 0.5 seconds as close as practical to the selected time at the end of which period the timing circuit stops the heating element breaking the ciruit thereto. At this point the timing circuit activates the digital readout circuit which then shows a reading of the actual current in millivolts flowing through the test cell.

Figure 6:
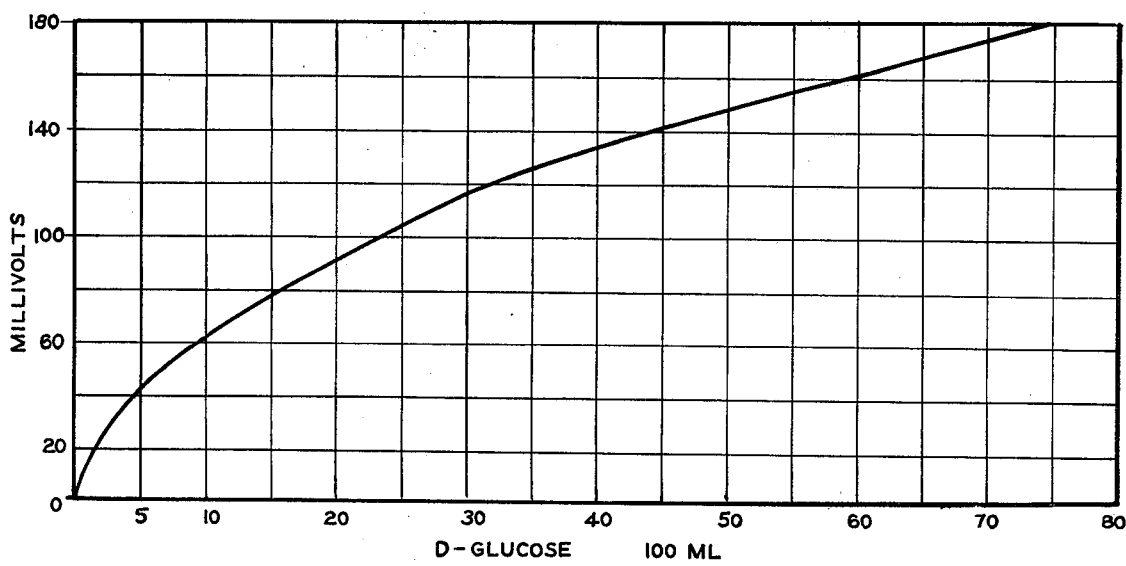
FIG. 6 is a plot showing the relationship of millivolts, vs. D-glucose.

As stated, other numerical indicia could be used to indicate the condition of the test cell. For instance, the cell could be activated to read the digits as 1, 2, 3 or 4; 1 indicating satisfactory;2 slightly raised glucose; 3 approaching the high side; and 4 dangerously high, whatever reading is of optimum significance to the user. Moreover, the digital reading modified to the curve of FIG. 6 can be modified to read in actual glucose content of any actual test sample. Again, since each body fluid may have its own typical glucose content significant of low, high or normal body conditions and each fluid has its own set of values, the readout indicia may be set to read accurately for the selected test fluid, for example saliva. Finally, since the glucose content of each body fluid of ten has its own range of glucose values, they nevertheless are related. For instance, if saliva glucose is high, the blood glucose would also be high and the readout indicia can be adjusted to read the glucose content of one fluid such as blood, when in fact another body fluid such as saliva is tested.

The digital millivolt meter is set on the 300 millivolt scale and operates under a condition of positive polarity. The maximum useful scale for the digital readout will be from minus 20 to plus 200 millivolts. The negative readability of the instrument allows calibration of the instrument for solution of 0 glucose content. It tends to show in which direction the instrument may be inaccurate, if it needs adjustment. For this purpose the instrument may have a negative polarity switch built in (not shown).

The electrode assembly encased in plastic as shown is quite durable and will readily withstand the selected temperature so that for this purpose other plastic bodies may be selected. Electrode assembly is easily accessible. It may be removed from its jack plug connectors 30 and 42 so that it is easily removed and cleaned after each test. The surface area of the exposed electrodes are selected to produce a millivolt potential for a typical test solution in a desired range; for instance, the copper electrode hereof may have an exposure of about 0.1 to 0.025 square inches and the platinum component may be a surface area ranging from 0.015 to 0.0025. Again, as shown in FIG. 2, the assembly may have a cylindrical outline and be sized to fit in a wide mouthed container 64 and supported therein for the tests.

The test solution, as indicated, is preferably a Benedict solution; and in one method of use, the Benedict solution, usually in small exactly measured quantities, will be selected and placed in a container 64. Thus, the container will be supplied with a standard quantity of test solution, usually about 2 to 4 ml. but variable in a useful practical range, as stated. While generally a 3 ml. standard solution will be used, it can vary in amount from 1 to 10 ml. The container will be sealed until ready for use.

The following table shows a Benedict solution in variable quantities in milligrams that would be filled into 1 to 10 ml. volume solutions for distribution as a standard solution in a container, 64.

| QUANTITATIVE BENEDICT SOLUTION (TABLET FORM) Tablet size (milliliters) | | | | | | | | | | |
|---|---|---|---|---|---|---|---|---|---|---|
| Chemical Components | | | | | | | | | | |
| (weights given in milligrams) | 1 | 2 | 3 | 4 | 5 | 6 | 7 | 8 | 9 | 10 |
| Crystallized Copper Sulfate $CuSo_4.5H_2O$ (mg.) | 18 | 36 | 54 | 72 | 90 | 108 | 126 | 144 | 162 | 180 |

-continued

QUANTITATIVE BENEDICT SOLUTION (TABLET FORM)
Tablet size (milliliters)

| Chemical Components | | | | | | | | | | |
|---|---|---|---|---|---|---|---|---|---|---|
| Anhydrous Sodium Carbonate $Na_2CO_3$ (mg.) | 100 | 200 | 300 | 400 | 500 | 600 | 700 | 800 | 900 | 1,000 |
| Potassium Citrate $K_3C_6H_5O_7 \cdot H_2O$ (mg.) | 200 | 400 | 600 | 800 | 1,000 | 1,200 | 1,400 | 1,600 | 1,800 | 2,000 |
| Potassium Thiocyanate KCNS (mg.) | 125 | 250 | 375 | 500 | 625 | 750 | 875 | 1,000 | 1,125 | 1,250 |
| Potassium Ferrocyanide $K_4Fe(CN)_6 \cdot 3H_2O$ (mg.) | 0.25 | 0.50 | 0.75 | 1.00 | 1.25 | 1.50 | 1.75 | 2.00 | 2.25 | 2.50 |
| TOTAL WEIGHT (milligrams) | 443.25 | 886.50 | 1,329.75 | 1,773.00 | 2,216.25 | 2,659.50 | 3,102.75 | 3,546.00 | 3,989.25 | 4,432.50 |

The user would merely break open the sealed cap of the standard container, taking the cap off and use it by inserting the electrode as shown in FIG. 2, heating for 15 seconds at 98°C and adjusting the voltage of the test apparatus to zero reading. Then there is added a measured quantity of test body fluid from a pipette, and then reinserting the electrode and activating the apparatus to heat the test solution at about 98°C for a timed period of about 15 seconds, the test results can be read automatically by the indicia 14 appearing on the millivolt meter. The test container 64, as stated, will preferably be sized to receive the selected quantity of Benedict solution, i.e., 1 to 10 ml., which quantity will generally about half fill the container. Moreover, the container will be sized with a large enough mouth to receive the electrode, usually in easy sliding fit therein with the lower end of the electrode immersed in the test solution to an intermediate depth.

Each container after test use will be disposed of entirely, whereby for each test a container is supplied with a fixed exact quantity of standard Benedict solution to which the readout signal or potential will be adjusted to zero ready for measurement of significant glucose contents of an added sampling of body fluid in quantity practical for this type of test. As stated, that solution may be varied over the range of 1 to 10 ml., but it usually will be about 2 to 4 ml. and the container correspondingly sized.

In an alternate procedure, the container is a standard test bottle or cup, either throw-away or one which may be reused after washing, and into which is pipetted a selected quantity of 2, 3 or 4 ml. of distilled water, and a preformed pill or tablet of the size needed to supply that quantity of liquid is dropped into the liquid to form a standard Benedict solution. While that amount of liquid may be accurately added by means of a pipette, the container itself may be marked to a quantitatively measured liquid level, and the liquid such as distilled water may be added thereto up to the graduation or mark on the container by the user.

Great accuracy is not needed for supplying the water since the exact quantity of oxidizing agent will be contained in the pill added thereto and an exact quantity of this oxidizing agent will be reduced by the body fluid. The reagent may thereby be disposed as solids, i.e., pills or tablets of a selected size. These sizes will contain quantities of Benedict components as stated in the above table, variable with the quantity of liquid to be added to the test container; a requisite number of tablets will be added to the quantity of water used, i.e., 1, 2 or 3 tablets for 1, 2 or 3 ml. of water supplied to the test container.

Figure 5:
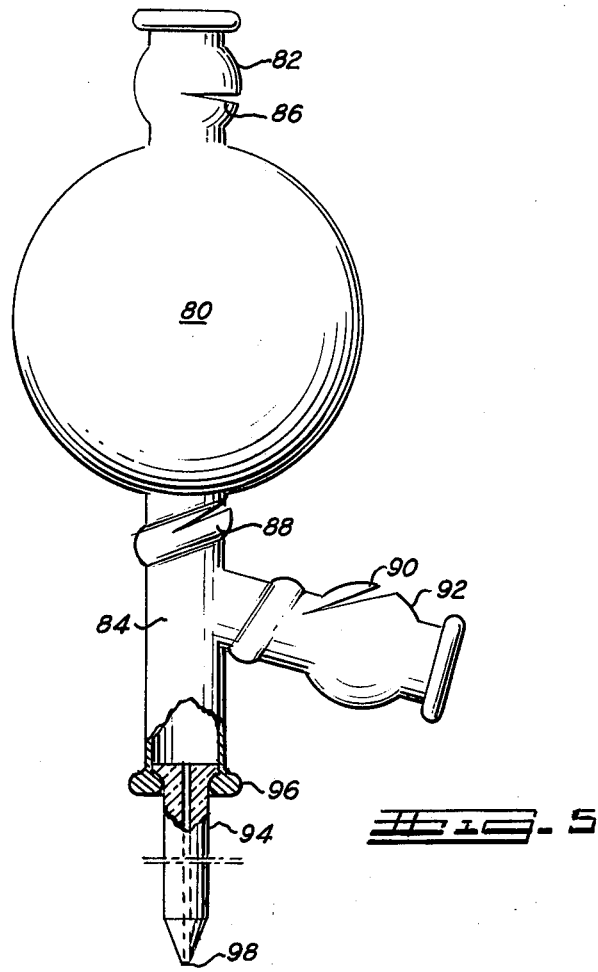
FIG. 5 shows a sampling pipette.

The test body fluid is measured in a pipette; for instance, a sample of saliva first expectorated into a separate container is taken up by a pipette, exactly calibrated, preferably as shown in FIG. 5 which is a filtering type. This pipette has a fine capillary tip slanted to a point which not only takes up a measured amount of test fluid, as a sampling for purposes of transfer of an exact quantity, but more important, the tip of the pipette having a diameter of from 0.1 to 0.005 microns is fine enough to filter out body solids or any thick phlegms from the test liquid, which may be associated therewith.

Referring to FIG. 5, a pipette has an aspirating bulb 80 leading into a thumb stopping valve 82 at the top and a long throat 84 at the bottom. There are three vents 86, 88 and 90, the latter disposed in a side bulb 92. Each vent is operable by closure with a thumb of the operator. The assembly is formed of natural rubber having sufficient rigidity to maintain its shape, but flexibly deformable readily by hand pressure. The throat portion 84 extends into a capillary tube 94 elastically sealed thereto by appropriate selections of dimensions of the tube 94 and throat 84 reinforced by a rubber ledge or rim 96. The lower glass or plastic tube 94 is graduated to fractions of a milliter, usually tenths of a millimeter, and the inner capillary is sized in the range stated above and terminates in a sharp angular tip 98 whereby to deflect any phlegm or solids from the test fluid into which the tip is inserted and prevents entry into the capillary. This effects filtration of solids and phlegm from the test fluid.

In operation, using the thumb and forefinger, the upper section 82 is grasped with the thumb closing the valve 86 and the remaining fingers squeezing the bulb 80 to expell air therefrom. The thumb and forefinger are then placed about the valves 88 and 90 to close this with the tip inserted in the test fluid and a filtered quantity of test fluid thereby is drawn up into the capillary tube 94 by release of compression of the bulb 80, thus aspirating an excess quantity of test fluid into the capillary tube 94. For expulsion of liquid with the thumb still closing the valve 88, the hand holding the valve 90 and pressing about the body of the bulb 92 compresses the same and expels air both from the bulb 92 and throat 84 to force liquid out of the capillary 94. That liquid is expelled first down to a selected marking from which to measure the amount actually being sampled, whereby the pipette carries the exact quantity of measured sampling of test fluid. The measured quantity of test liquid in the pipette is then transferred to the test flask 64, and the expulsion of test liquid contained in the pipette is continued to expel the exactly measured contents thereof into the test solution 68.

In normal use the device in FIG. 1 is switched to the on position by switch 69 illuminating the lamp 71 to indicate that the device is operative. A flask as shown in FIG. 3 having 3 ml. of Benedict solution, according to the composition of the above table, to which an additional 1 ml. of water is added, is placed in the test chamber of the device. The activated circuit heats the solution which is brought to a boil and allowed to boil for the measured time, such as 15 seconds as set by the timer. The electrode is inserted and the potentiometer adjusted whereby the millivolt meter will read zero for the total output of the circuit. Another test solution of 3 ml. of Benedict solution is prepared and to which 1 ml. of saliva as test sample is added by pipette as described above. The solution is again placed in the test camber, brought to a boil, heated for a time period of 15 seconds, and the electrode implaced will give a millivolt reading which now will be a measure of the glucose content of the saliva.

After that reading, the device is opened, raising the cover 16. The electrode is withdrawn from the jack plug contacts 30 and 42 and removed from the container 64. The container and its contents may then be disposed of, usually by throwing away. The electrode assembly 21 is washed and dried, ready for the next use.

While, as described, it is useful to make up the Benedict components in tablet or pill form, each of measured quantity, whereby one pill can be added to a 1 ml. test solution for converting the same to a standard Benedict solution of that volume. The pill size can be varied so that one or two pills could be used in simple units, easily handled. Any variation of the standard concentration can be accommodated by modifying the corresponding millivolt output of the modified Benedict solution residue, so that it will be adjusted to be readable still in terms of the original glucose content of the sample tested, while measuring it with the millivolt output of the cell determined upon the residual reaction product solution. Again, a 2 ml. test solution would have twice as much Benedict reagent as a 1 ml.; and a 3 ml. three times as much, etc.; modified possibly as stated above. It may be useful, as indicated, rather than making up a single large pill, varied in size to the unit test quantity, to make the Benedict tablet as a unit size, one for each milliliter standard solution; for example, one would add three of the pills or tablets to form a standard test solution thereof to the 3 ml. of distilled water.

The present test method is also applicable to measure the quantity or concentration level of other components of the body fluid. For instance, the glucose component of the body fluid may be bound, pre-oxidized selectively, sequestered, or converted to an inert form, inert to further reaction with test reagents. For instance, a test sampling may first be treated with a corresponding amount of formaldehyde which would bind the glucose to a fixed stable form inert to typical oxidizing and reducing agents, such as cupric sulfate, i.e., Benedict solution, phosopho-molybdic acid, iodine and methanol, sulfuric acid and ethanol, or pyrogallol. These are active to oxidize or reduce other components of the body test fluid, for instance, uric acid or the body hormone level, so that upon inactivating the glucose, the concentration level of these other body components can be similarly measured, following the same method as described above for glucose. That is, the body fluid will first have the glucose bound or inactivated so that the glucose contained in the body fluid will not respond to oxidizing or reducing agents as listed, and the addition of such reagents to the glucose bound body fluid will oxidize or reduce the other body fluid components therein. The redox potential then will be measured for the body fluid sampling in which the glucose was bound, removed or inactivated so that the reading of the millivolt meter will be in terms of the other oxidizable or reducible components of the body fluid. That reading can be for the total content of the blood or other body fluid of oxidizable or reducible components, or it can be for one or more of them; and again, where a lower level component, such as a hormone, is to be measured in content, then the other body fluid components which might interfere are each removed or inactivated. For instance, both glucose and uric acid can be inactivated or removed before testing other body fluid components such as the hormone in the test sample. For this purpose, it may also be useful to calibrate the millivolt meter or to use a more sensitive millivolt meter readable in microvolts; that is, one more sensitive to a smaller electrode potential change.

Thus, the present method is useful for testing of the various other body fluids listed, and with a suitable modified procedure can test one or more body fluid components in a sequence or as a single component which is oxidizable or reducible, and from which the glucose or other interfering component has been removed or inactivated.

Moreover, the present method can be applied to test minute components present in other liquids, such as the impurities in water. For instance, it can be used to measure oxidizable components, i.e., organic components or inorganic salts contained as impurities in the water; or it can be used to measure reducible components such as dissolved oxygen contained in water. For this purpose, again the apparatus is set to a null voltage using a standard solution of oxidizing or reducing agent and a small exactly measured quantity of sampling, that is, impure water, typically 1 cc., is exactly pipetted into the test solution and then reacted with the standard solution of oxidizing or reducing agent and the redox potential is then read for the cell in which the reaction solution may be directly indicative of the impurity content of the water.

The following example illustrates the practice of this invention:

EXAMPLE I

A stock solution of glucose was made in concentration of one gram of anhydrous glucose dissolved in 100 milliliters of distilled water. The stock solution was diluted to about 30 milligrams per hundred to a series of known glucose concentration and the emf was measured by the test procedure outlined above, whereby graphically the output of the cell was readable in terms of milligrams of glucose for a fixed quantity of test solution, i.e., 3 milliliters. The read out of the millivolt meter was then adjusted numerically to read the milligrams of glucose variable accurately with the actual millivolt output of the cell. Thereafter in a typical test, using 3 ml. of Benedict solution as the test solution, and adding thereto one milliliter of saliva, heating the solution to a boil for a period of exactly 15 seconds, the readout of the millivoltage available in terms of milligrams of glucose can be directly readable from the instrument. Obviously this is a negative reading because all of the glucose has been oxidized and the actual reaction solution itself having the reduced copper content is the electrolyte resulting from oxidation of the fixed amount of glucose in the specific sample of saliva tested.

In an alternate procedure, the 3 ml. of test solution are modified to use 3 ml. of distilled water to which a pill corresponding to the 3 ml. standard Benedict solution, as described in the above table, was supplied, having the components of that table intermixed as the composited test solution containing 54 milligrams of copper sulfate pentahydrate; 300 milligrams of anhydrous sodium carbonate; 600 milligrams of potassium citrate; 375 milligrams of potassium thiocyanate; 0.75 milligrams of potassium ferrocyanide. The total weight of the pill was 1329.75 milligrams. The pill is preferably dissolved in the distilled water by dropping into the water supplied first to the container and before insertion about the standard electrode assembly.

The heating device actually heats to about 550°C and takes about three minutes to bring the test sample to a boil and is available commercially as a THERMOLYNE HOT PLATE sold by the Thermolyne Corporation, a subsidiary of Sybron Corporation.

The rectifier and filter circuit is 110 volt AC to 1½ volt DC sold by the Hewlitt-Packard power supply, set to 10 volts DC adjusted to read 1.5 volts on the output meter. The digital millivolt meter is standard laboratory supply with a variable range of 1 to 3000 millivolts with an accuracy of plus or minus 1% of full scale on any range, readily available commercially from numerous sources.

Other modifications will occur to those skilled in the art and, accordingly, it is intended that the description given herein is by way of illustration and not limiting except by the claims.

It will be understood that the test method apparatus and appurtenances described may be used chemically for testing body fluid of healthy, as well as diseased individuals, whereby normal health as well as diseases are indicated by normal and abnormal levels of such body fluid components as glucose, uric acid, hormones, etc., contained in the body fluid. Specifically, a high or low glucose level may be indicative of high or higher glycemia.

What is claimed is:

1. Process for measuring the concentration of reactable components in the body fluid such as glucose in terms of the residual redox potential of a primary cell, comprising reacting a measured sampling of human body fluid to be tested with at least one standard solution containing a measured excess quantity of reducible copper salt reagent under fixed reaction temperature conditions to react with a reactive component such as glucose of the body fluid contained in the test sample, and then measuring the redox potential developed by the reagent left in the reacted solution acting as the electrolyte of a primary cell as an indication of the quantity of the reacted components that was present in the test sample.

2. Process for measuring the glucose level of body fluids in terms of the residual redox potential of a primary cell, comprising oxidizing a measured sampling of human body fluid to be tested with a standard solution containing an excess quantity of a reducible copper salt as oxidizing agent at a selected high temperature for a short fixed period of time to oxidize glucose contained in the test sample, and then measuring the quantity of glucose in the test sample in terms of the residual redox potential developed by the reagent left in the reacted solution acting as the electrolyte of a primary cell as an indication of the quantity of the reacted components that was present in the test sample.

3. The method as defined in claim 2 wherein the body fluid tested is a member of the group consisting of saliva, spinal fluid, perspiration, tears, blood, plasma and urine.

4. The method as defined in claim 3 wherein the redox potential output of said cell is connected to a millivolt meter to be visibly readable as output voltage of said cell, said output voltage being modified to read in terms of the glucose level of said body fluids other than the fluid actually tested.

5. The method as defined in claim 4 wherein the body fluid tested is saliva and the output voltage of said cell is modified to read in terms of the corresponding glucose levels in blood.

6. The method as defined in claim 2 wherein the body test fluid is first purified before testing.

7. The method as defined in claim 2 wherein the test fluid is a measured quantity of saliva.

8. The method as defined in claim 2 wherein the standard solution is a standard Benedict solution.

9. The method as defined in claim 2 wherein the test solution is a standard Benedict solution made up and sealed in containers of test quantity size as an excess of said reagent ranging from 1 to 10 ml., the said containers having a wide mouth and sized to receive a test electrode assembly, a body fluid samplings, and said standard solution for effecting the reaction.

10. The method as defined in claim 2 wherein the standard solution is a measured quantity of distilled water in the range of 1 to 10 ml. to which is added sufficient solid Benedict reagent in dry tablet form to form a standard Benedict solution in the selected quantity of water.

11. The method as defined in claim 1 wherein the temperature of the reacting solution is fixed at a raised point above ambient.

12. The method as defined in claim 11 wherein the fixed raised temperature is the boiling point of the reaction solution.

13. The process for measuring the concentration of reactable components in a body fluid other than glucose in terms of the residual redox potential of a primary cell comprising first reacting said body fluid with a reagent selective to bind the glucose content to inactive form, and then reacting under fixed reaction temperature conditions a measured sample of said human body fluid to be tested with at least one standard solution containing a measured excess quantity of reagent reactable with at least one of the remaining body fluid components of said sample, and measuring the level of said remaining components in the sample in terms of the residual redox potential developed by the reagent left in the reacted solution acting as the electrolyte of a primary cell as an indication of the quantity of the reacted components that was present in the sample.

* * * * *